United States Patent
Chamberlin et al.

(10) Patent No.: US 9,500,585 B2
(45) Date of Patent: Nov. 22, 2016

(54) PHOTOMETER AND METHOD FOR COMPENSATING FOR AMBIENT TEMPERATURE CHANGES IN A PHOTOMETER

(71) Applicant: Spectro Scientific, Inc., Chelmsford, MA (US)

(72) Inventors: David B. Chamberlin, Shelton, CT (US); Michael Edward Glowinski, Ridgefield, CT (US); Donald Stanton Lavery, Chrisfield, MD (US)

(73) Assignee: Spectro Scientific, Inc., Chelmsford, MA (US)

(*) Notice: Subject to any disclaimer, the term of this patent is extended or adjusted under 35 U.S.C. 154(b) by 274 days.

(21) Appl. No.: 14/515,644

(22) Filed: Oct. 16, 2014

(65) Prior Publication Data

US 2016/0109366 A1    Apr. 21, 2016

(51) Int. Cl.
*H01J 40/14* (2006.01)
*G01N 21/59* (2006.01)

(52) U.S. Cl.
CPC ....... *G01N 21/59* (2013.01); *G01N 2201/1211* (2013.01)

(58) Field of Classification Search
CPC .............................. G01N 21/00; G01N 21/274
USPC .......... 250/214 R, 214 A, 214 C, 352, 338.1, 250/338.3
See application file for complete search history.

(56) References Cited

U.S. PATENT DOCUMENTS

| | | |
|---|---|---|
| 2,648,249 A | 8/1953 | Canada |
| 3,818,198 A | 6/1974 | Walker et al. |
| 3,937,962 A | 2/1976 | Faulhaber et al. |
| 3,999,069 A | 12/1976 | Taylor et al. |
| 4,441,023 A | 4/1984 | Doctor et al. |
| 4,605,905 A | 8/1986 | Aslan |
| 4,792,682 A | 12/1988 | Endou et al. |
| 4,943,800 A | 7/1990 | Ikeda et al. |
| 4,967,082 A | 10/1990 | Cooke et al. |
| 5,041,723 A | 8/1991 | Ishida et al. |
| 5,118,947 A | 6/1992 | Hamashima et al. |
| 5,734,165 A | 3/1998 | Unal et al. |
| 5,834,776 A | 11/1998 | Beratan et al. |
| 6,420,708 B2 | 7/2002 | Wilks, Jr. et al. |

(Continued)

FOREIGN PATENT DOCUMENTS

AU    199883779 B2    1/1999

OTHER PUBLICATIONS

P.A. Wilks, "In-Line Infrared Sensors Covering the Mid Infrared From 2 to 14 um (5000 to 700 cm-1)", Vibrational Spectroscopy-Based Sensor Systems, 2002, pp. 76-82, Proceedings of SPIE vol. 4577.

*Primary Examiner* — Kevin Pyo
(74) *Attorney, Agent, or Firm* — Iandiorio Teska & Coleman, LLP (57) ABSTRACT

A photometer and associated method includes a source of radiation to be directed through a sample and a detector stage configured to measure radiation after passing through the sample. A voltage follower circuit is connected to the detector and is configured to provide an output signal which varies as a function of the detector output voltage and which varies as a function of the ambient temperature. A processing subsystem is configured to determine a temperature compensation factor from the voltage follower circuit output signal.

29 Claims, 7 Drawing Sheets

(56) References Cited

U.S. PATENT DOCUMENTS

| | | | |
|---|---|---|---|
| 6,515,285 B1 * | 2/2003 | Marshall | G01J 5/20 250/339.03 |
| 6,730,909 B2 | 5/2004 | Butler | |
| 7,281,809 B2 | 10/2007 | Warren | |
| 7,618,188 B2 | 11/2009 | Glaser et al. | |
| 8,074,324 B2 | 12/2011 | Warren et al. | |
| 8,183,513 B2 | 5/2012 | Hanson et al. | |

* cited by examiner

PHOTOMETER AND METHOD FOR COMPENSATING FOR AMBIENT TEMPERATURE CHANGES IN A PHOTOMETER

FIELD OF THE INVENTION

The subject invention relates to photometers.

BACKGROUND OF THE INVENTION

In a photometer used to measure, for example, soot levels in lubrication oils, the amount of oil in waste water, and the like, a source directs infrared radiation through a sample and to one or more detectors. See, for example, U.S. Pat. Nos. 2,648,249; 3,937,962; 3,818,198; 5,041,723; 5,734,165; and 6,420,708 incorporated herein by this reference and P. A. Wilks "In-line Infrared Sensors Covering the Mid Infrared from 2 to 14 μm (5000 to 700 cm$^{-1}$)", Vibrational Spectroscopy-Based Sensor Systems, Steven D. Christesen, Arthur J. Sedlacek III, Editors, Proceeding of SPIE Vol. 4577 (2002), also incorporated herein by this reference.

Pyroelectric detector elements may be placed on top of the base of a TO can package and each detector element is associated with a different filter. See also U.S. Pat. No. 4,943,800 incorporated herein by the reference. In operation, a pyroelectric detector responds to a temperature change caused by incident infrared radiation from the source passing through the sample by generating a small electric charge. If, for example, oil in a water sample absorbs radiation at the wavelength $\lambda_{oil}$ and a pyroelectric detector is filtered such that only wavelength $\lambda_{oil}$ reaches the detector, the $\lambda_{oil}$ wavelength radiation will not reach the pyroelector detector and it will not generate an electric charge (or it will generate a lesser charge). But, since the pyroelectric detector responds to any changes in temperature, a change in the ambient temperature will cause the output of the pyroelectric detector to change resulting in an erroneous reading.

To account for fairly large ambient temperature changes, a temperature probe (e.g., a thermistor) can be attached to the TO can and changes in ambient temperature can be compensated for during calibration of the photometer.

SUMMARY OF THE INVENTION

In some fields and uses of a photometer, it is desirable to detect substances present in a sample down to the parts per million level or even sub parts per million accuracy. One example is at offshore drilling rigs where water used in the drilling process is delivered back into the ocean. The water is filtered after use and sampled to detect oil still present in the wastewater. It is desirable that the photometer used to sample the wastewater is very accurate and can detect even very small amounts of oil.

When a thermistor is attached to the detector TO can, the resulting accuracy is not high enough for such applications. For example, the temperature at the location of the thermistor could be different than the temperature at another location on the TO can or different than the temperature of an individual pyroelectric detector element. Different pyroelectric detector elements, for example, may be at different temperatures. Moreover, a thermistor can typically only be used to compensate for large environmental temperature changes on the order of 1-25 Kelvin. Further if the design of the photometer only is such that the source and detector are mounted co-linearly with no further attempt to direct the incident radiation through the sample and into the detector, it is often the case that a significant amount of radiation passing through the sample will not reach the detector (e.g., 20-80%) resulting in a loss of sensitivity. By using a waveguide, transmission efficiency can be significantly enhanced. Furthermore the waveguide can ensure that the radiation profile is matched to the detector.

In this invention, the temperature of an individual pyroelectric detector may be measured electronically to account for even small changes in ambient temperatures as opposed to changes in temperature caused by incident radiation, thus resulting in a highly stable and sensitive photometer system.

U.S. Pat. Nos. 5,118,947; 7,618,188; 3,999,069; 4,792,682; 4,605,905; 4,441,023; 8,183,513; 6,730,909; and 4,967,082 incorporated herein by reference purport to teach means of temperature compensation but do not teach an overall compensation process for using ambient temperature as provided herein.

Also, a waveguide which maximizes signal throughput acts in concert to produce maximum signal-to-noise ratio capabilities to enable the analysis of trace impurities in a fairly simple photometer system.

A photometer, in one example, includes a source of radiation to be directed through a sample, and a detector stage configured to measure radiation after passing through the sample. The detector stage may include at least one detector outputting a voltage in response to radiation incident on the detector and a voltage follower circuit connected to the detector and configured to provide an output signal which varies as a function of the detector output voltage and which varies as a function of the ambient temperature. A processing subsystem is configured to determine a temperature compensation factor from the voltage follower circuit output signal.

In some examples, the detector stage includes a filter for the detector. A detector stage may include a plurality of detectors and a plurality of filters and there may be a voltage follower circuit for each detector.

In one example, the voltage follower circuit includes a transistor located proximate the detector. The voltage follower circuit may include a transistor having a gate connected to the detector output voltage and a source connected to the processing subsystem and outputting a signal including an AC signal and an offset voltage. Here, the voltage follower circuit may further include a gate resistor connected between the transistor gate and ground and/or a source resistor connected between the transistor source and ground. There may be an analog to digital converter between the transistor source and the processing subsystem.

The processing subsystem may include filter logic configured to filter the offset voltage. Preferably, the source of radiation is pulsed at a frequency and the filter logic is configured to filter signals greater than and less than that frequency. The processing subsystem may further be configured to determine the amplitude of the AC signal, for example, by applying a Fourier transform to the AC signal. The processing subsystem may further be configured to determine the offset voltage level, for example, by averaging the transistor source signal over time. The processing subsystem may be configured to determine the temperature compensation factor as a function of any change to the amplitude of the AC signal and the offset voltage.

In one design, the source of radiation is on one side of the sample and the detector stage is on the opposite side of the sample. In another design, the source of radiation is at one end of a crystal, the detection stage is at an opposite end of the crystal and the sample is located adjacent the crystal. There may be a light pipe between the source and the detector. In one example, the light pipe tapers to match the configuration of the detector stage.

The photometer may further include a temperature sensor associated with the detector stage and the processing subsystem is then configured to determine a temperature compensation factor from the temperature sensor.

Also featured is a method of compensating for ambient temperature changes for a photometer. The method may include pulsing a source of radiation at a frequency, detecting radiation passing through a sample using a voltage follower circuit connected to a detector, and determining a temperature compensation factor from the voltage follower circuit output signal. An offset voltage is filtered from the voltage follower circuit output signal, the amplitude of the filtered voltage follower circuit output signal is determined, and the offset voltage level is determined.

Filtering the offset voltage may include filtering any signals in the voltage follower circuit output signal greater than or less than said source of radiation pulsing frequency. The temperature compensation factor may be a function of the offset voltage level and the amplitude of the filtered voltage follower circuit output signal. The method may further include detecting the temperature of the detector and inferring another temperature compensation factor from the detected temperature.

Also featured is a method of compensating for ambient temperature changes in a photometer. One method includes connecting a detector to the gate of a transistor and configuring the transistor source to provide an output signal including an AC detector signal and an offset voltage. The offset voltage is used to determine temperature changes of the transistor resulting in transconductance changes of the transistor. The determined temperature change is used to calculate a temperature compensation factor to be applied to said AC detector signal.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features, and advantages will occur to those skilled in the art from the following description of a preferred embodiment and the accompanying drawings, in which.

DETAILED DESCRIPTION OF THE INVENTION

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Figure 1:
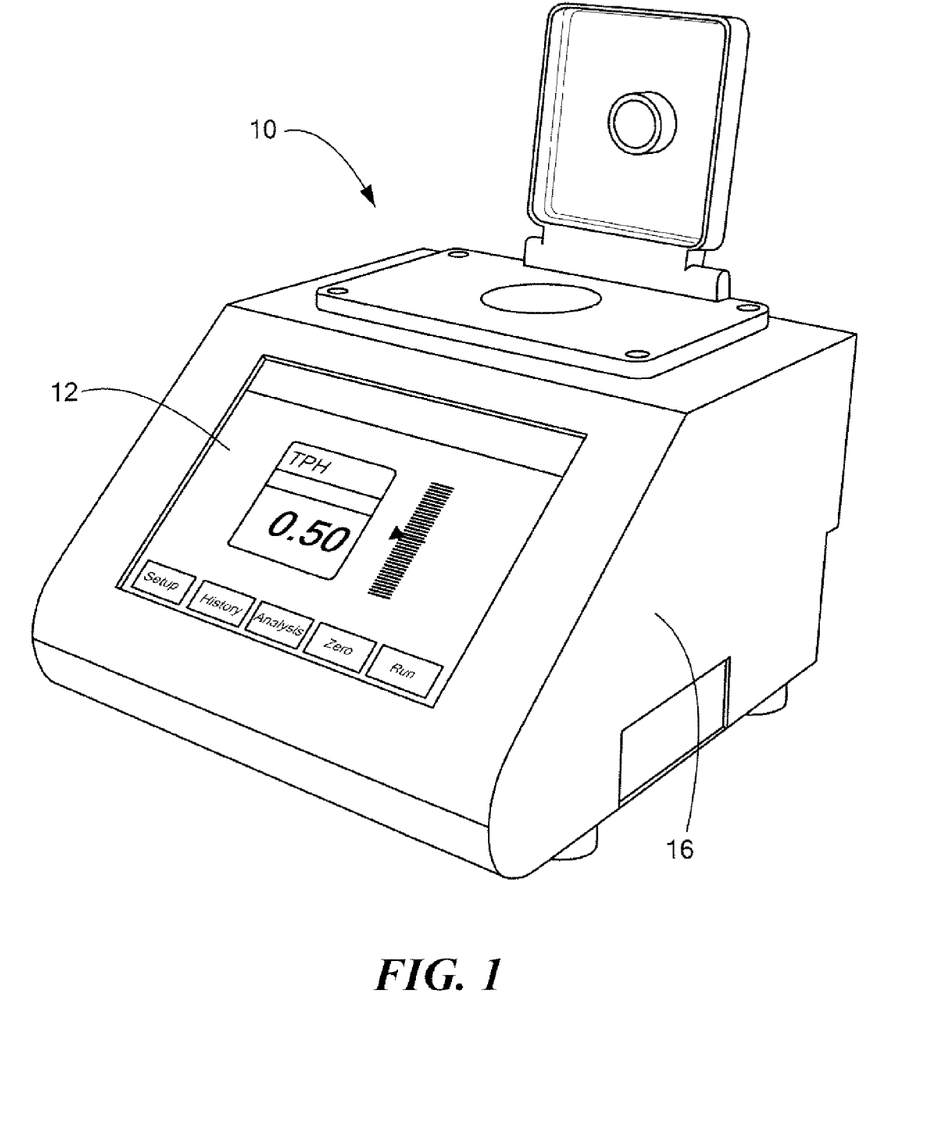
FIG. 1 is a schematic three dimensional front view showing an example of a photometer in accordance with the invention.

FIG. 1 shows an example of a photometer 10 with input/output section 12 (e.g., including a touch screen). Photometer 10 can be used to test a sample and to very accurately report, for example, the amount of oil in a water sample. Preferred is a system which can detect very small (e.g., parts per million) oil in a water sample.

Figures 2, 3:
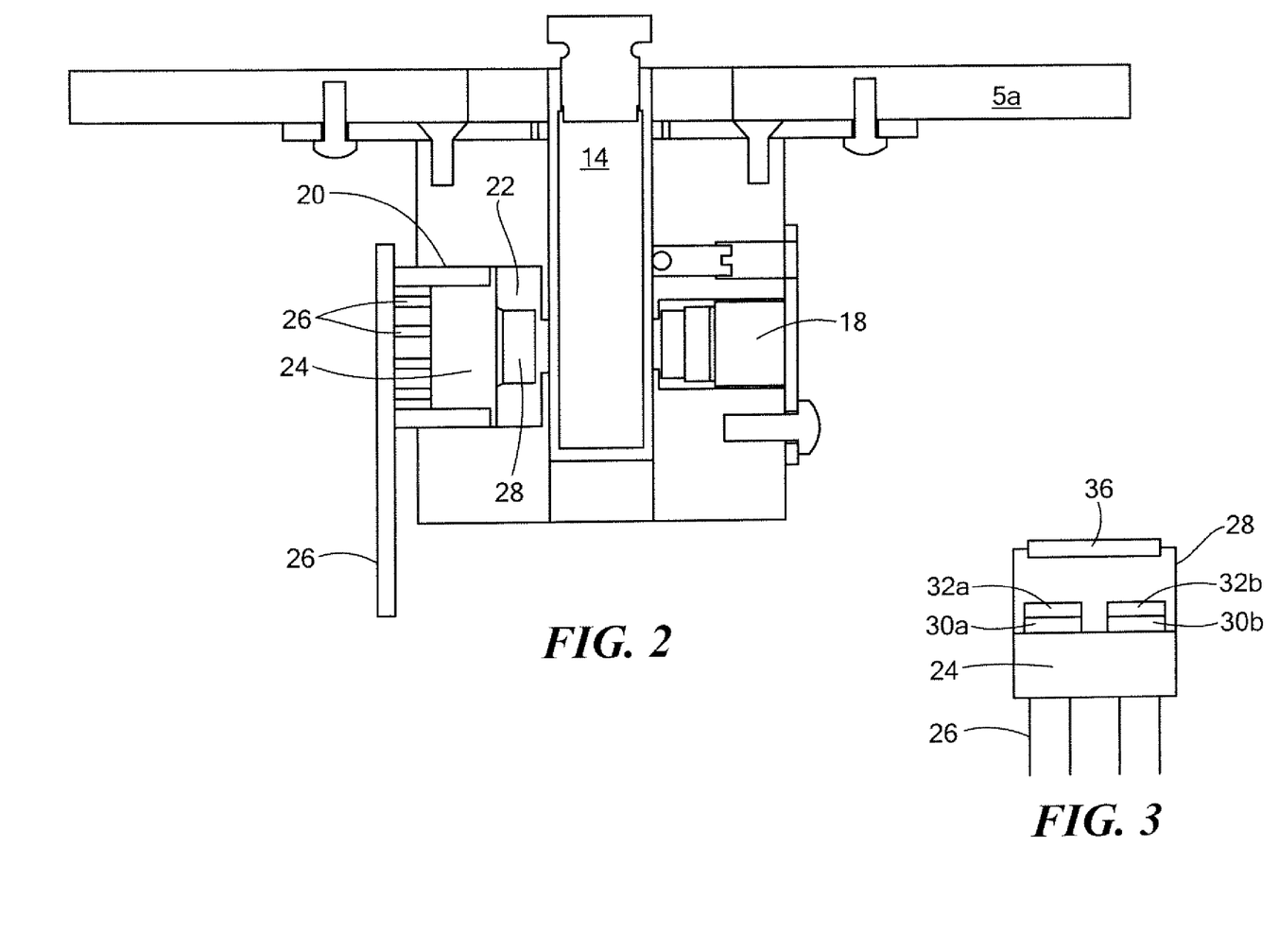
FIG. 2 is a schematic cross sectional front view showing, in one example, the primary components associated with the photometer shown in FIG. 1.
FIG. 3 is a schematic cross sectional front view showing the primary components associated with one example of the detector stage of FIG. 2.

FIG. 2 shows an example where a sample is placed in sample holder 14 (e.g., a 10 mm cuvette). Inside housing 16, FIG. 1 is an infrared radiation source 18, FIG. 2, for example an Axetris 600.347 on one side of the sample and detector stage 20 configured to detect and measure radiation from the infrared source 18 after passing through the sample in sample holder 14.

In the example, detector stage 20 includes TO can 22 with a base 24 having leads 26 connected to printed circuit board 26. As shown in FIG. 3, TO base 24 may include one or more detectors 30a, 30b mounted thereon each having a different filter 32a. Note that such a filter can also be tunable over a wavelength range of interest (e.g., 8-9 μm). The filters are configured to filter out specific wavelengths for elements or compounds of interest. TO can cover 28 hermetically seals the detectors and filters and includes window 36 for passing incident radiation to the detectors. In one example, there is only one detector. In other examples, there are four or more detectors. See also U.S. Pat. No. 4,934,800 incorporated herein by this reference.

Figure 4:
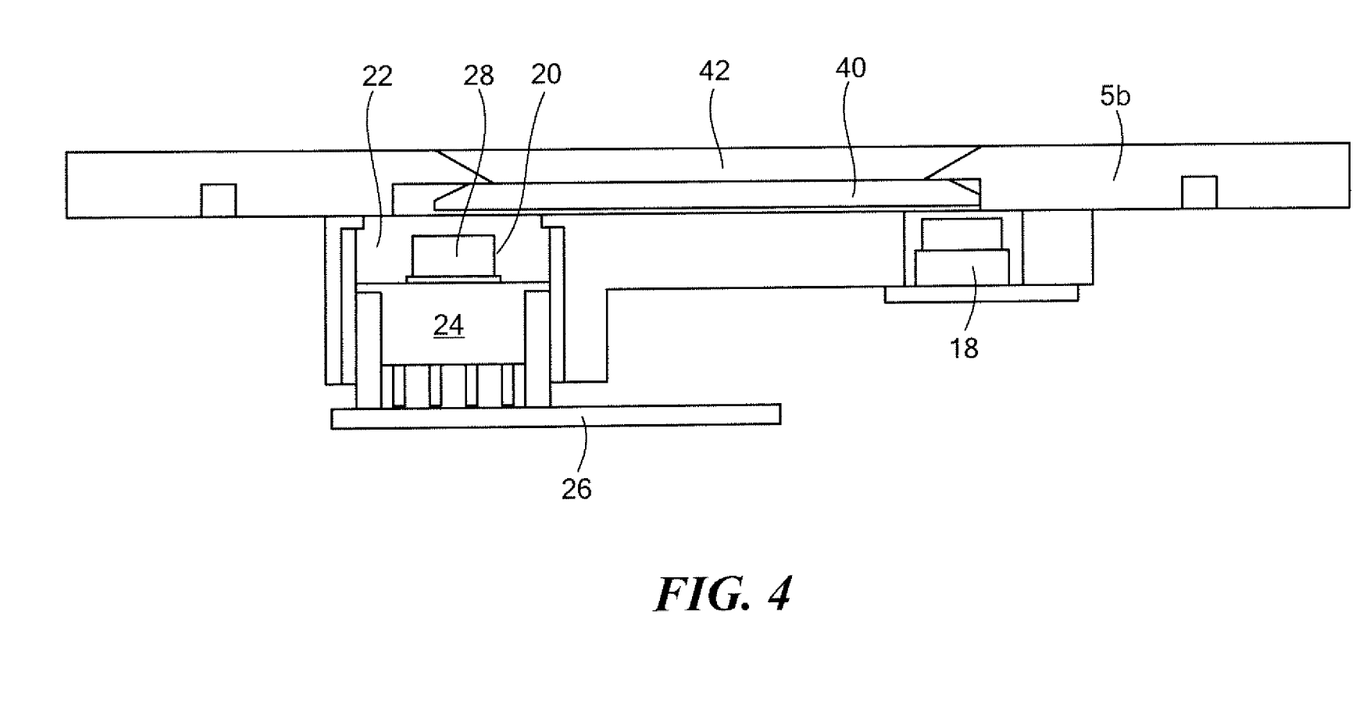
FIG. 4 is a schematic cross sectional front view showing another arrangement of the primary components associated with the photometer shown in FIG. 1.

In another example, infrared source 18, FIG. 4 is located proximate one end of attenuated total reflectance (ATR) crystal 40 and detector stage 20 is located proximate the other end of crystal 40. A sample is presented to trough 42 adjacent crystal 40. See, for example U.S. Pat. No. 6,420,708 incorporated herein by the reference. Note the interchangeable sample stage top plates 5a, FIGS. 2 and 5b, FIG. 4 in a given unit housing (e.g., 16, FIG. 1).

In some examples, there is a waveguide/light pipe (for example, a ZnSe waveguide) used to collect radiation transmitted through a sample and to distribute the radiation equally across multiple detectors. In the example shown in FIG. 5, the detector stage 20' includes a package 50 with a linear array of detectors 30a, 30b, and 30c and the like and ZnSe tapered light pipe 60 is configured to receive radiation passing through the sample at broad end 62 and then tapering as shown to match the configuration of detectors 30. In one example, light pipe 60 was 1.4 inches long, broad end 62 was round and 0.5 inches in diameter, and the taper at 61a and 61b resulted in rectangular distal face 64 (also see FIG. 6) 0.130 inches wide by 0.512 inches tall. There may be an anti-reflective coating on entrance and exit faces 62 and 64. Package 50 may include therein a printed circuit board with a processing subsystem electronics (including an application specific integrated circuit, microprocessor, or similar processing circuitry).

A light pipe for the configuration with detectors mounted on a TO can base would taper to a round exit face with a diameter matching the configuration of the detector(s) on the TO can.

The detectors used are typically pyroelectric elements (e.g., comprised of lithium tantalate). One detector may be used as a reference (drift detection) detector and filtered or blocked so it does not receive incident radiation.

Figure 7:
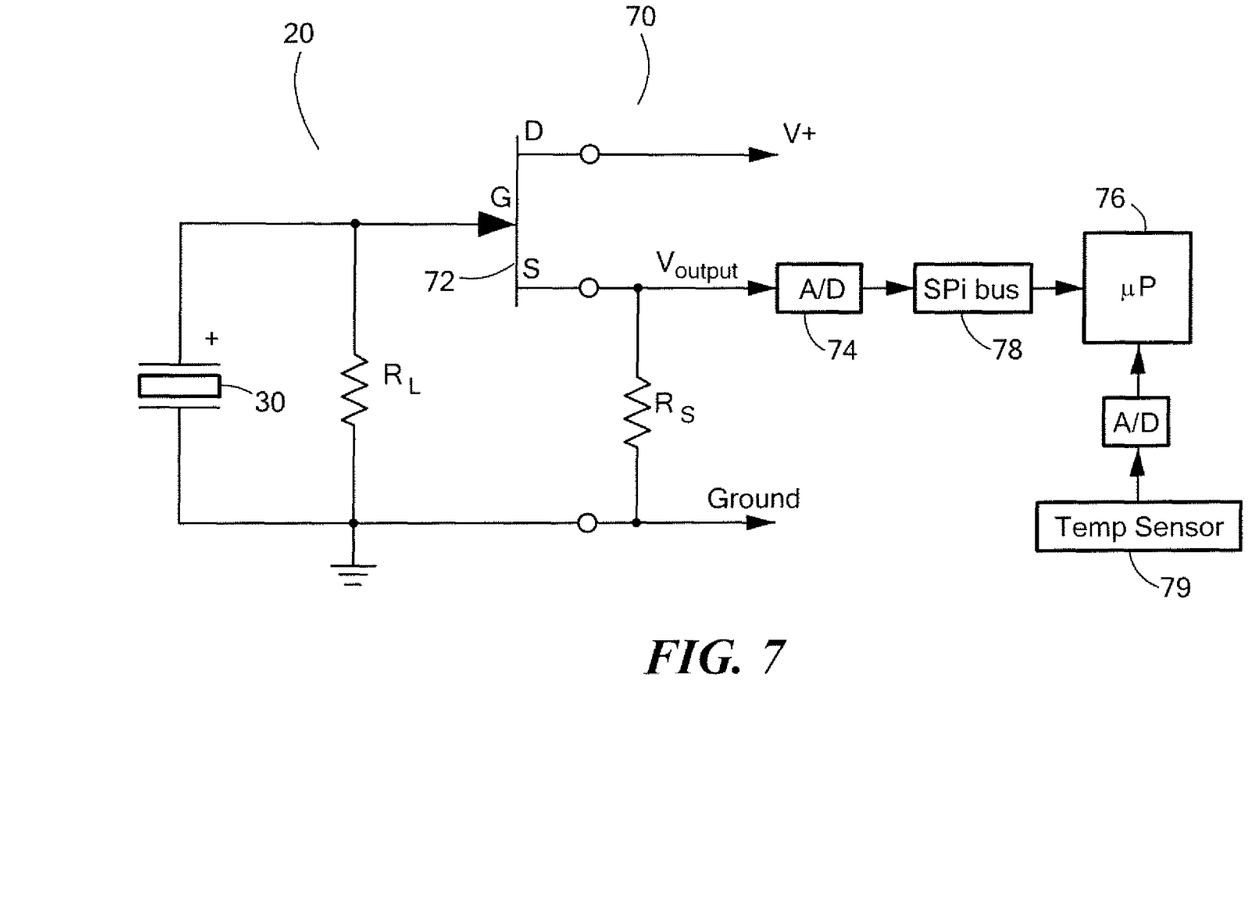
FIG. 7 is a circuit diagram showing, in one example, the primary components associated with the detector stage of the photometer embodiments of FIGS. 2, and 4.

As shown in the example of FIG. 7, one preferred detector stage includes pyroelectric element 30 which outputs a voltage signal in response to radiation incident on the detector delivered to a voltage follower circuit 70 here in this example including junction gate field effect transistor 72 the gate of which is connected to detector 30 across gate resistor $R_L$ (e.g., $6.5 \times 10^{10}$ ohms). The output of the transistor ($V_{output}$) is used to determine the amount of radiation detected by the detector and to then determine the quantity of various elements, substances, and/or contaminants in the sample. The drain is connected to voltage V+ (e.g., 5.0-7.0 V).

JFET 72 may be disposed inside TO can 22, FIG. 2-4, for example closely adjacent the detectors on the TO base but preferably shielded from any incident infrared radiation. There may further include a connection between the gate resistor and the source pin on the JFET to increase the output signal.

Figures 5, 6:
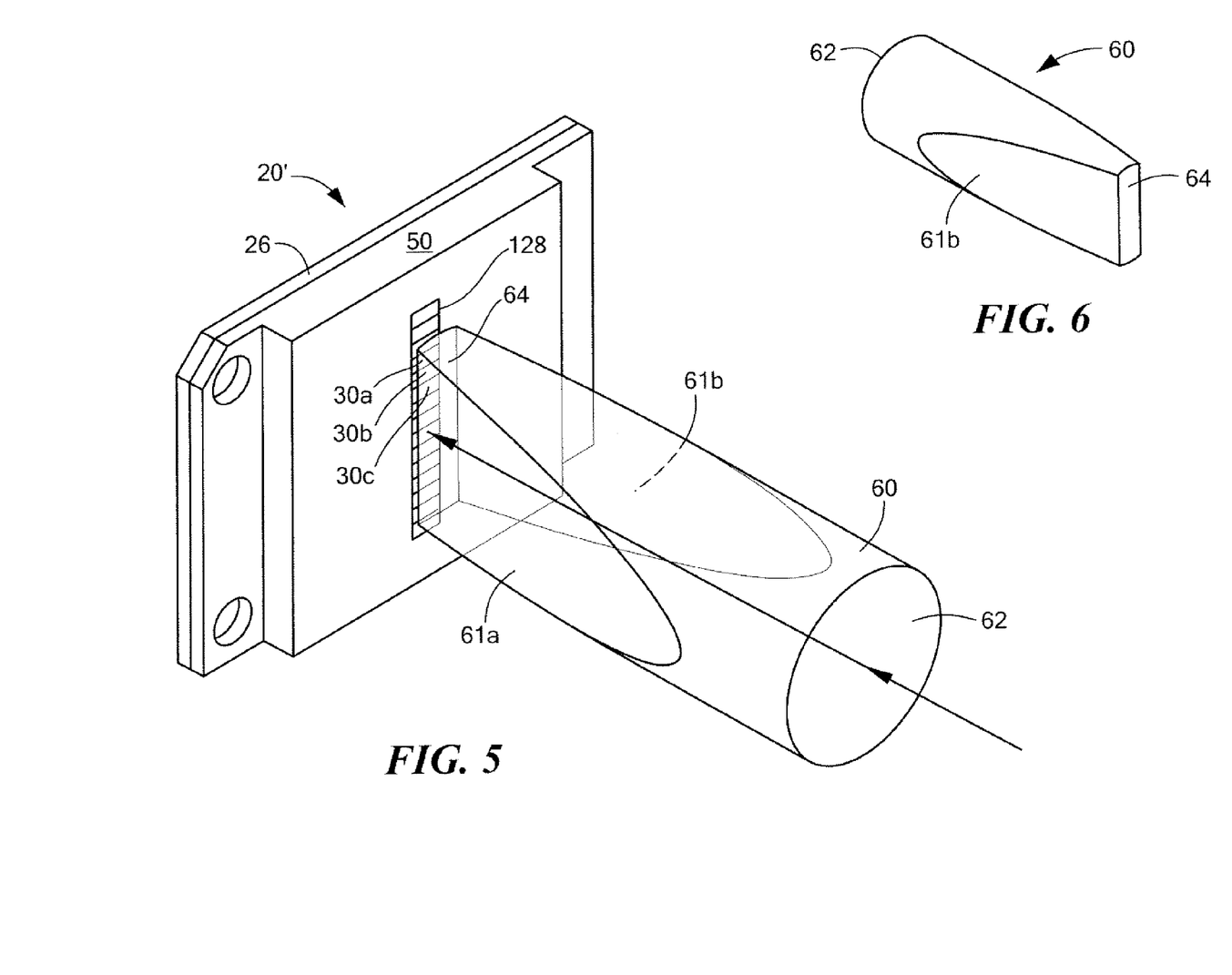
FIG. 5 is a schematic view showing an example of a tapered light pipe used in conjunction with a detector stage including a detector package with a linear array of detector elements.
FIG. 6 is a schematic front view showing the distal end of the light pipe of FIG. 5.

Here, the JFET is used as a voltage follower to provide a relatively low impedance to the external circuitry located, for example, on printed circuit board 26, FIGS. 2, 4 and 5. The JFET produces a voltage $V_{output}$ across external resistor $R_S$ (e.g., 39K ohms) which includes two components: an offset voltage and the AC detector signal. The output voltage of the JFET ($V_{output}$) produced across resister $R_S$ is delivered to analog to digital converter 74 connected to microprocessor 76 via SPI bus 78. Processor 76, bus 78, and $R_S$ are typically included on printed circuit board 26, FIGS. 3, 4, and 5. Microprocessor 76 may also receive a signal from a temperature sensor 79 mounted proximate the detectors (e.g., on or inside the TO can). Microprocessor 76 may include an analog to digital converter for converting the temperature sensor signal to a digital signal for processing. Or, an external analog to digital converter may be used.

Figure 8A:
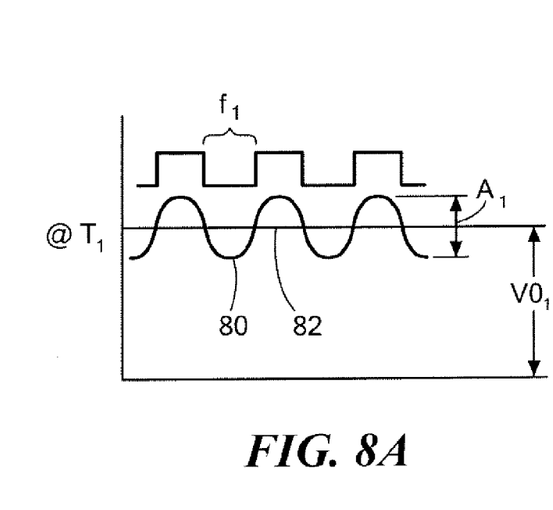
FIG. 8A is a graph showing the output of the field effect transistor of FIG. 7 depicting the combination of the detector AC signal and the offset voltage at one ambient temperature.
Figure 8B:
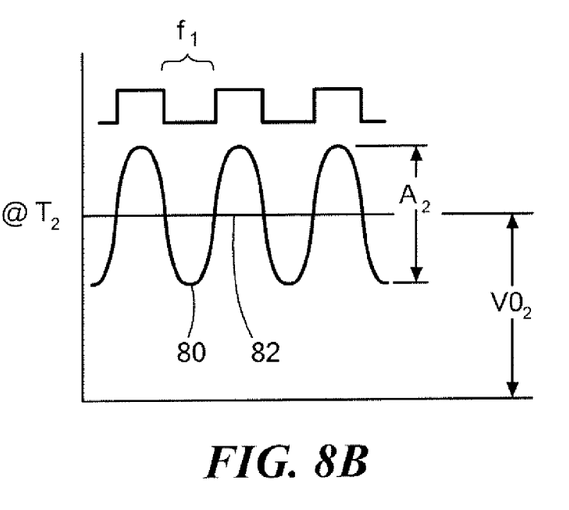
FIG. 8B is a graph showing the changes to the AC detector signal and the offset voltage due to an ambient temperature change.

FIGS. 8A-8B shows the JFET $V_{output}$ signal composed of the detector AC signal 80 and the offset voltage 82 at two different ambient temperatures $T_1$ and $T_2$. Here, the sample has not changed and the radiation source output at frequency $f_1$ has not changed. All that has changed is the ambient temperature and yet the amplitude of the detector AC signal 80 reported by the JFET and $R_S$ has amplitude $A_1$ at temperature $T_1$ and amplitude $A_2$ at temperature $T_2$. The offset voltage has also changed from $VO_1$ at temperature $T_1$ to $VO_2$ at temperature $T_2$. In some aspects of the invention, this change in the offset voltage can be used to calculate a temperature compensation factor applied to AC signal amplitude $A_2$ to report a correct amplitude of $A_1$ thus resulting in a much more accurate photometer (e.g., sensitive to one part per million level accuracies) even if $T_1$ and $T_2$ do not differ significantly.

Figure 9:
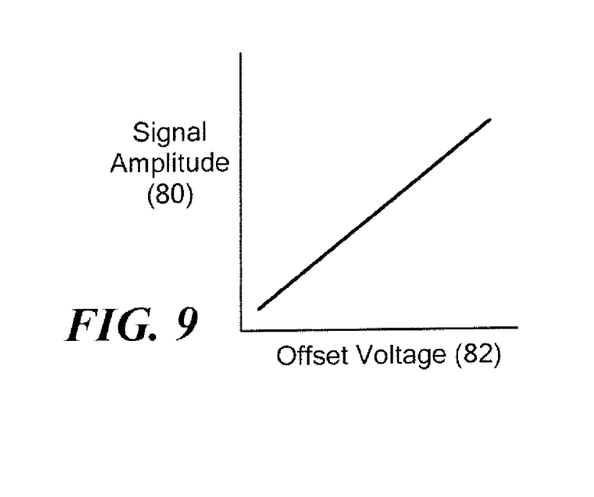
FIG. 9 is a graph showing the linear relationship between the detector AC signal amplitude and the offset voltage over small variations in temperature.

In the invention, it was discovered that over a relatively small temperature change range, the detector AC signal amplitude varied linearly with the offset voltage as shown in FIG. 9.

The offset voltage is produced by the transconductance of the conductive channel in the JFET 72, FIG. 7 with $V_{GS}<0$. When properly biased, the JFET acts as a constant current source producing a relatively constant offset voltage across $R_S$ of typically 1-3 volts. The AC detector signal is produced by the small changes in gate voltage caused by temperature changes in the pyroelectric element. As the JFET gate voltage changes, the depletion region of the JFET increases and decreases, changing the transconductance of the JFET thereby producing a small signal change in voltage across $R_S$. The magnitude of this signal is proportional to the rate of change in temperature of the pyroelectric element and is superimposed on the offset voltage.

Since the pyroelectric element responds to any changes in temperature, a change in the environmental temperature will cause a change in the AC detector signal voltage to change that can be indistinguishable from the external changes in radiation impinging on the detector element. It is desirable to compensate for these environmental temperature changes so that the radiation from the source can be accurately measured.

Although biased as a constant current source, the transconductance of the JFET itself changes with the temperature of the JFET body and it is this characteristic that can be used to compensate for temperature fluctuations of the pyroelectric detector element. The change in transconductance is relatively linear over small temperature changes. Since the JFET is typically in good thermal contact with the detector element inside the TO can, the change in offset voltage becomes a good indicator of small changes of temperature inside the TO can.

One preferred temperature compensation method typically includes two measures of environmental temperature. The offset voltage described above is used to measure and compensate for small changes in temperature inside the pyroelectric detector TO can and a separate temperature probe (usually a thermistor) which is in close proximity to the TO can mounting is used to measure and compensate for large environmental temperature changes. The temperature compensation factors can be derived by monitoring the AC signal voltage, the offset voltage, and the thermistor output signal as the environment changes in temperature (with the external source of radiation held at a constant level).

Regression analysis of this data can then be used to derive the temperature compensation factors: one for the offset voltage and one for the thermistor temperature. For linear regression, the offset compensation factor is the slope of the offset voltage vs. AC signal shown in FIG. 9. Likewise, the thermistor compensation factor is the slope of the thermistor temperature vs. the signal. A zero reading can be taken which records the offset voltage and thermistor temperature at a reference point in time. The compensation factors may be multiplied by the difference between the measured reading and the zero reading of both offset voltage and thermistor temperature and then subtracted from the signal. This compensates the signal voltage for large and small fluctuations in environmental temperature.

Figure 10:
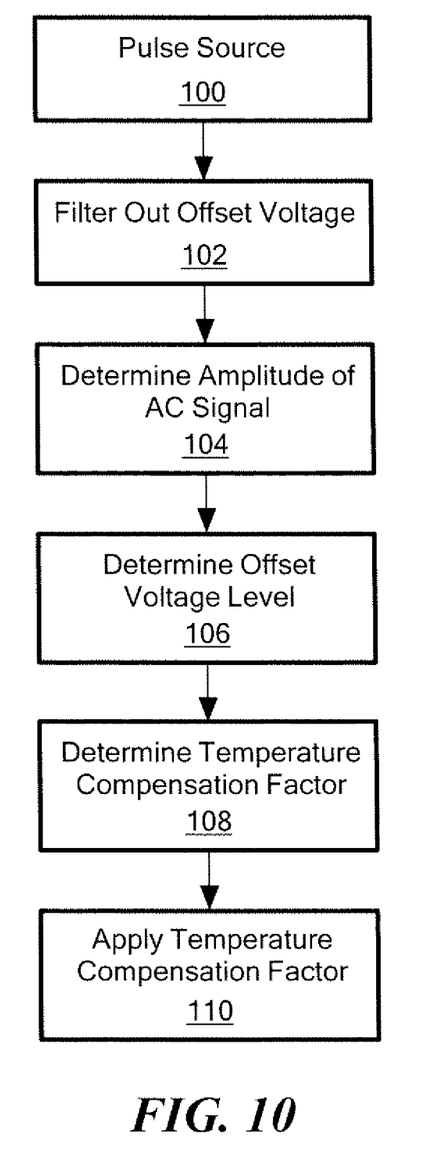
FIG. 10 is a flow chart depicting the primary steps associated with the programming of the microprocessor of FIG. 7 and also depicting the primary steps associated with a method in accordance with an example of the invention.

Microprocessor 76, FIG. 7 may be programmed to include filter logic (e.g., an FIR filter) configured to filter the offset voltage $V_0$ from the $V_{output}$ signal, FIGS. 8A-8B. Since the infrared source is pulsed at frequency $f_1$ (e.g., 10 Hz), the filter logic may filter out frequencies in $V_{output}$ less than or greater than 10 Hz which produces then only AC signal 80. Pulsing the infrared source and filtering out the offset voltage are shown at steps 100 and 102 in FIG. 10.

The amplitude A of the filtered AC signal is then detected and determined, step 104, using, for example, a digital Fourier transform logic employed by microprocessor 76, FIG. 7. The offset voltage level is then determined, step 106, FIG. 10 preferably by averaging the $V_{output}$ signal over a very long time (e.g., much longer than the frequency f) to eliminate the AC signal 80, FIG. 8. From these values, a temperature compensation factor can be determined, step 108, FIG. 10.

In some examples, a given offset voltage can be set to a zero level and then different offset voltage levels are compared to the zero level to calculate an offset voltage to be multiplied by the slope of the line in FIG. 9 (AC signal amplitude verses offset voltage) to arrive at a compensation factor. Microprocessor 76, FIG. 7 then increases or decreases the AC amplitude determined in step 104, FIG. 10 by the compensation factor, step 110, FIG. 10.

This method could be performed for each detector element if multiple detectors each have their own JFET voltage follower circuitry. Alternatively, a compensation factor calculated for one detector element could be applied to the other detector elements.

For larger ambient temperature changes, the microprocessor may use the output of the temperature sensor 79, FIG. 7 mounted on or in the TO can to calculate a correction factor to be applied to the measured AC signal amplitude especially in regions where the relationship shown in FIG. 9 is not linear.

The result is a new photometer (e.g., filtometer) apparatus sensitive to parts per million accuracy.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant cannot be expected to describe certain insubstantial substitutes for any claim element amended.

Other embodiments will occur to those skilled in the art and are within the following claims.

What is claimed is:

1. A photometer comprising:
   a source of radiation to be directed through a sample;
   a detector stage configured to measure radiation after passing through the sample, the detector stage including:
      at least one detector outputting a voltage in response to radiation incident on the detector, and
      a voltage follower circuit connected to the detector and configured to provide an output signal which varies as a function of the detector output voltage and which varies as a function of the ambient temperature; and
   a processing subsystem configured to determine a temperature compensation factor from the voltage follower circuit output signal.

2. The photometer of claim 1 in which the detector stage includes a filter for said detector.

3. The photometer of claim 2 in which the detector stage includes a plurality of detectors and a plurality of filters.

4. The photometer of claim 3 in which there is a voltage follower circuit for each detector.

5. The photometer of claim 1 in which the voltage follower circuit includes a transistor located proximate the detector.

6. The photometer of claim 1 in which the voltage follower circuit includes a transistor having a gate connected to the detector output voltage and a source connected to the processing subsystem and outputting a signal including an AC signal and an offset voltage.

7. The photometer of claim 6 in which the voltage follower circuit further includes a gate resistor connected between the transistor gate and ground.

8. The photometer of claim 6 in which the voltage follower circuit further includes a source resistor connected between the transistor source and ground.

9. The photometer of claim 6 further including an analog to digital converter between the transistor source and the processing subsystem.

10. The photometer of claim 6 in which the processing subsystem includes filter logic configured to filter the offset voltage.

11. The photometer of claim 10 in which the source of radiation is pulsed at a frequency and the filter logic is configured to filter signals greater than and less than said frequency.

12. The photometer of claim 10 in which the processing subsystem is further configured to determine the amplitude of the AC signal.

13. The photometer of claim 12 in which the processing subsystem is configured to determine the amplitude of the AC signal by applying a Fourier transform to the AC signal.

14. The photometer of claim 12 in which the processing subsystem is further configured to determine the offset voltage level.

15. The photometer of claim 14 in which the processing subsystem is configured to determine the offset voltage level by averaging the transistor source signal over time.

16. The photometer of claim 14 in which the processing subsystem is configured to determine the temperature compensation factor as a function of any change to the amplitude of the AC signal and the offset voltage.

17. The photometer of claim 1 in which the source of radiation is on one side of the sample and the detector stage is on the opposite side of the sample.

18. The photometer of claim 1 in which the source of radiation is at one end of a crystal, the detection stage is at an opposite end of the crystal, and the sample is located adjacent the crystal.

19. The photometer of claim 1 further including a light pipe between the source and the detector.

20. The photometer of claim 19 in which the light pipe tapers to match the configuration of the detector stage.

21. The photometer of claim 1 further including a temperature sensor associated with the detector stage and the processing subsystem is configured to determine a temperature compensation factor from the temperature sensor.

22. A method of compensating for ambient temperature changes for a photometer, the method comprising:
pulsing a source of radiation at a frequency;
detecting radiation passing through a sample using a voltage follower circuit connected to a detector; and
determining a temperature compensation factor from the voltage follower circuit output signal by:
filtering an offset voltage from the voltage follower circuit output signal,
determining the amplitude of the filtered voltage follower circuit output signal, and
determining the offset voltage level.

23. The method of claim 22 in which filtering the offset voltage includes filtering any signals in the voltage follower circuit output signal greater than or less than said source of radiation pulsing frequency.

24. The method of claim 22 in which the amplitude of the filtered voltage follower circuit output signal is determined by applying a Fourier transform to the filtered voltage follower circuit output signal.

25. The method of claim 22 in which determining the offset voltage level includes averaging the voltage follower circuit output signal over time.

26. The method of claim 22 in which the temperature compensation factor is a function of the offset voltage level.

27. The method of claim 26 in which the temperature compensation factor is a function of the offset voltage level and the amplitude of the filtered voltage follower circuit output signal.

28. The method of claim 22 further including detecting the temperature of the detector and inferring a temperature compensation factor from the detected temperature.

29. A method of compensating for ambient temperature changes for a photometer, the method comprising:
connecting a detector to the gate of a transistor and configuring the transistor source to provide an output signal including an AC detector signal and an offset voltage;
using the offset voltage to determine temperature changes of the transistor resulting in transconductance changes of the transistor; and
using said determined temperature change to calculate a temperature compensation factor to be applied to said AC detector signal.

* * * * *